United States Patent
Cao et al.

[19]

[11] Patent Number: 6,158,984
[45] Date of Patent: Dec. 12, 2000

[54] ROTARY BLOOD PUMP WITH CERAMIC MEMBERS

[75] Inventors: Hengchu Cao, Roseville; David M. Lancisi, Folsom, both of Calif.

[73] Assignee: Kriton Medical, Inc., Sacramento, Calif.

[21] Appl. No.: 09/221,094

[22] Filed: Dec. 28, 1998

[51] Int. Cl.[7] .............................. F04B 17/00; A61M 37/00
[52] U.S. Cl. .................. 417/423.1; 417/53; 417/423.1; 604/265; 416/241 B; 415/200
[58] Field of Search ................... 604/265; 417/423.7, 417/423.1, 423.12, 423.4, 53; 415/200, 206, 900, 196, 197; 416/241 B

[56] References Cited

U.S. PATENT DOCUMENTS

| | | | |
|---|---|---|---|
| 5,079,467 | 1/1992 | Dorman | 310/156 |
| 5,092,879 | 3/1992 | Jarvik | 623/3 |
| 5,290,227 | 3/1994 | Pasque | 600/16 |
| 5,332,374 | 7/1994 | Kricker et al. | 417/420 |
| 5,443,503 | 8/1995 | Yamane | 623/3 |
| 5,507,629 | 4/1996 | Jarvik | 17/356 |
| 5,549,667 | 8/1996 | Davidson | 623/3 |
| 5,692,882 | 12/1997 | Bozeman, Jr. et al. | 417/45 |
| 5,713,730 | 2/1998 | Nose et al. | 417/423.12 |
| 5,803,720 | 9/1998 | Ohara et al. | 417/420 |
| 5,810,758 | 9/1998 | Yamazaki et al. | 604/4 |
| 5,840,070 | 11/1998 | Wampler | 604/131 |
| 5,851,174 | 12/1998 | Jarvik et al. | 600/16 |
| 5,928,131 | 7/1999 | Prem | 600/16 |

FOREIGN PATENT DOCUMENTS 0 291 780  11/1988  European Pat. Off. .

*Primary Examiner*—Charles G. Freay
*Assistant Examiner*—Robert Z. Evora
*Attorney, Agent, or Firm*—George H. Gerstman; Seyfarth, Shaw

[57] ABSTRACT

An implantable rotary blood pump including a rotor mounted for rotation within a pump housing. The rotor has a shaft portion and an impeller carried by the shaft portion. A rotor motor is provided, with a motor including a plurality of permanent magnets carried by the impeller and motor stators on opposite sides of the impeller. Structural members are provided between the impeller and stators to provide structural support and hermetical sealing. The structural members comprise biocompatible, corrosion resistant, electrically non-conducting ceramic material, which alleviate eddy current losses.

20 Claims, 1 Drawing Sheet

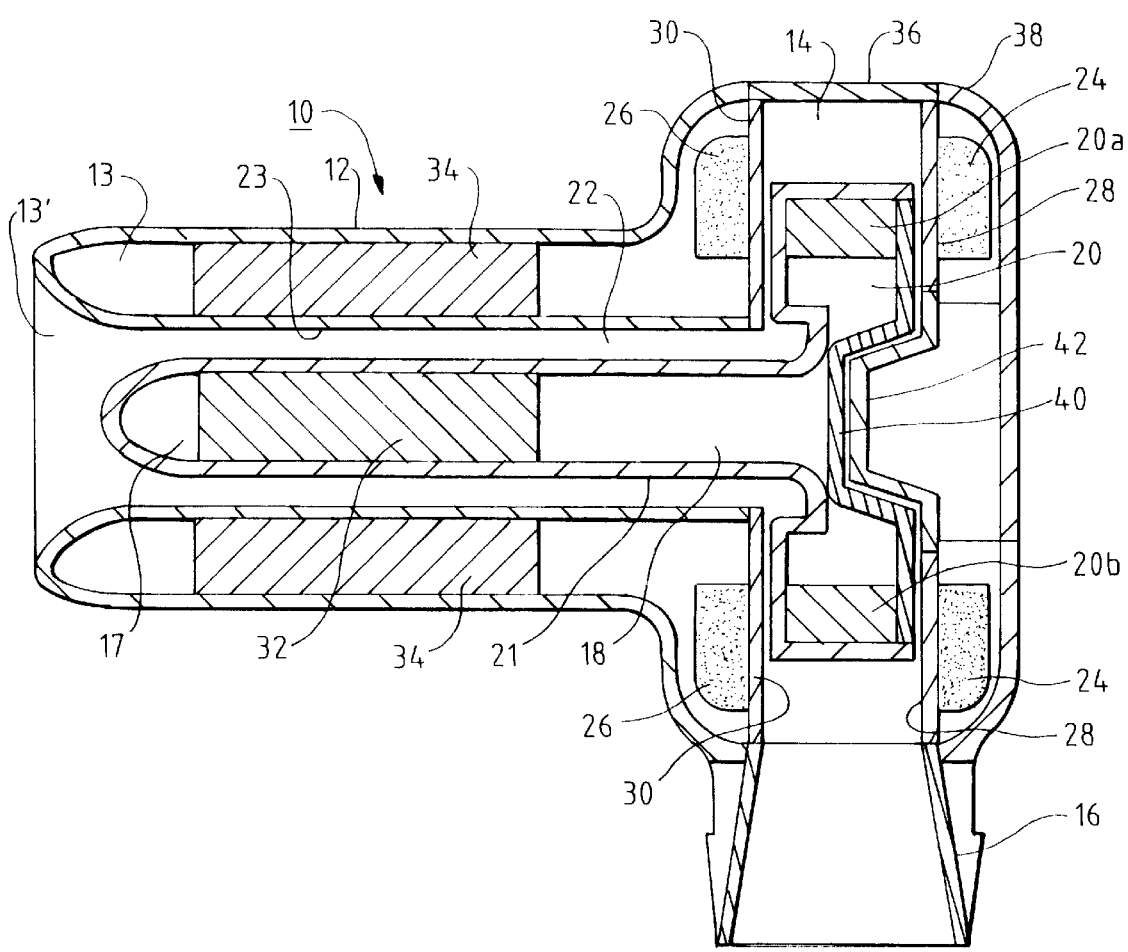

ROTARY BLOOD PUMP WITH CERAMIC MEMBERS

FIELD OF THE INVENTION

The present invention concerns blood pumps. More specifically, the invention pertains to continuous flow pumps of rotary design, which may be suitable for implantation in humans, for use as chronic ventricular assist devices.

BACKGROUND OF THE INVENTION

In Wampler U.S. Pat. No. 5,840,070, a continuous flow pump of rotary design is disclosed, suitable for implantation in humans, for use as a chronic ventricular assist device. The disclosed device uses passive, magnetic radial bearings to maintain an impeller and its support shaft for rotation about an axis, thus eliminating the necessity for a drive shaft seal.

In the FIGS. 11–14 embodiment of Wampler U.S. Pat. No. 5,840,070, the disclosure of which is incorporated herein, the implantable heart pump utilizes two stators, each on opposite sides of the impeller and each having a number of stator coils and pole pieces. Thus the driving mechanism involves electromagnetic coupling between the permanent magnets in the impeller and the driving coils in the stators. It has been found desirable to provide a structural member between the impeller and stators to provide structural support and hermetical sealing. It is desirable for this structural member to be biocompatible, non-thrombogenic and corrosion resistant. There have been considerations of forming these structural members of metal, such as titanium or titanium alloy, or cobalt-chromium-nickel alloy. However, it has been found that the time varying magnetic field in the structure arising from the rotating magnets induces eddy currents in the metal structure, causing energy loss. In addition, such eddy current loss also produces heat dissipation, which may result in blood damage, thrombosis and thromboembolism.

It is, therefore, an object of the present invention to provide a rotary blood pump in which eddy currents such as those induced in a metal structure, are alleviated.

Another object of the present invention is to provide a rotary blood pump having an electromagnetically coupled driving mechanism with structural support and hermetical sealing between the impeller and the stator.

A still further object of the present invention is to use ceramic components in an electromagnetically driven blood pump to improve energy efficiency and biocompatibility.

An additional object of the present invention is to provide a novel blood pump which is sufficiently compact to be implantable in the human body and which uses ceramic components to provide strategic advantages.

A further object of the present invention is to provide a novel rotary blood pump that is small, light, simple in construction, and relatively easy to manufacture.

Other objects and advantages of the present invention will become apparent as the description proceeds.

SUMMARY OF THE INVENTION

In accordance with the present invention, a rotary blood pump is provided. The pump comprises a pump housing and a motor mounted for rotation within the housing. The rotor has a shaft portion and an impeller carried by the shaft portion. A rotor motor is provided. The motor includes a plurality of permanent magnets carried by the impeller and a motor stator located within the housing. A structural member is positioned between the impeller and the stator, comprising a biocompatible, corrosion resistant ceramic material.

In the illustrative embodiment, the ceramic material is selected from the group consisting of aluminum oxide, zirconium oxide, yttria partial stabilized zirconia, magnesia-partial-stabilized zirconia, ceria-partial-stabilized zirconia, titanium oxide, magnesia, zirconia-toughened alumina, ruby, sapphire, single crystal alumina, cubic zirconia, quartz, fused silica, silicon nitride and aluminum nitride.

In the illustrative embodiment, the rotary blood pump housing is sufficiently compact to be implantable in a human body. The pump includes radial magnetic bearings carried by the shaft portion and radial magnetic bearings carried by the housing. The structural member provides structural support and hermetical sealing, and utilizes non-thrombogenic and electrically non-conductive ceramic materials.

In the illustrative embodiment, the pump housing also comprises ceramic material such as pyrolytic carbon. The impeller includes an impeller housing having a journal bearing surface and the pump housing has a journal bearing surface for cooperating with the impeller housing journal bearing surface.

In accordance with the present invention, a method is provided for reducing eddy current losses in a rotary blood pump. The method comprises the steps of providing a pump housing; providing a rotor for rotation within the housing, the rotor having a shaft portion and an impeller carried by the shaft portion; providing a rotor motor which includes a plurality of permanent magnets carried by the impeller and a motor stator; and positioning between the impeller and the stator a structural member comprising a biocompatible, corrosion resistant ceramic material.

A more detailed explanation of the invention is provided in the following description and claims, and is illustrated in the accompanying drawing.

BRIEF DESCRIPTION OF THE DRAWING

The FIGURE is a longitudinal, cross-sectional view of an implantable blood pump constructed in accordance with the principles of the present invention.

DETAILED DESCRIPTION OF THE ILLUSTRATIVE EMBODIMENT

Referring to the drawing, an electromagnetically driven ventricular assist device or blood pump 10 is illustrated. Electromagnetically driven blood pumps have the advantage of compact size and energy efficiency compared to pneumatic or hydraulic driven systems. Blood pump 10 is preferably sufficiently compact to be implantable in the human body. The pump is of any rotary design, including but not limited to centrifugal, axial flow, or hybrid flow designs.

The preferred embodiment illustrated herein utilizes two stators, each on opposite sides of the impeller and each having a number of stator coils and pole pieces. An example of an implantable heart pump with two stators is the FIGS. 11–14 embodiment of Wampler U.S. Pat. No. 5,840,070, the disclosure of which is incorporated herein. It is understood, however, that no limitation is intended with respect to the particular heart pump to which the present system is applicable.

As illustrated in the FIGURE, rotary blood pump 10 includes a forward pump housing 12 having radial magnetic bearings in the form of ring magnets 34 carried by forward housing 12, surrounding an elongated inlet tube 13 with an entry end 13' and an impeller casing or a volute 14. A discharge tube 16 communicates with the interior periphery of casing 14. Tube 16 has a tangential orientation with respect to the radius of the casing 14, for effectively channeling the blood output from the pump.

A pump rotor 17 is located within housing 12 and includes a support shaft 18 attached to an impeller 20. Impeller 20, support shaft 18 and rotor 17 have an impeller housing 21. There is a blood flow path 22 between rotor 17 and the inner sidewalls 23 of inlet tube 13.

Rotor 17 is mounted for rotation about a longitudinal axis which extends both through shaft 18 and impeller 20. Impeller 20 has a number of blade sectors that are relatively thick in the axial direction. The thick impeller 20 has the ability to utilize permanent magnetic pieces 20a and 20b and others, that are inserted in a manner enabling a pair of stators 24 and 26 to be on opposite sides of the impeller 20. A first motor stator 24, comprising conductive coils and pole pieces is located at the rear of impeller 20 on a structural member 28. A second motor stator 26, comprising windings and pole pieces, is positioned on the forward side of impeller 20 on structural member 30. Although (for simplicity) only two coils are illustrated on each side of the impeller in the FIGURE, it is to be understood that it is preferred that six windings and pole pieces be on each side of the impeller although other arrangements may be utilized as desired.

Magnetic bearings in the form of permanent core magnets 32 are provided on the rotor 17 and the magnetic bearings in the form of ring magnets 34 are carried by the housing for levitating rotor 17 and maintaining it in proper radial alignment with respect to its longitudinal axis.

Forward housing 12 is contiguous with a housing portion 36, which is contiguous with back housing cover 38. The housings 12, 36 and 38, impeller housing 21, structural members 28 and 30, and discharge tube 16, are preferably formed of corrosion resistant ceramic materials. For example, structural members 28 and 30, which separate the impeller from the stator, are made of biocompatible, non-thrombogenic, electrically non-conducting and corrosion resistant ceramic materials, such as aluminum oxide, zirconium oxide, yttria partial stabilized zirconia, magnesia-partial-stabilized zirconia, ceria-partial-stabilized zirconia, titanium oxide, magnesia, zirconia-toughened alumina, ruby, sapphire, single crystal alumina, cubic zirconia, quartz, fused silica, silicon nitride and aluminum nitride. These ceramic materials have excellent biocompatibility and corrosion resistance in implant applications. Since the electrical resistivity is extremely high compared with metals, the eddy current related electrical power loss is minimal. The hermeticity of the ceramic containing structures can be maintained by bonding ceramic member to metal alloy by brazing, soldering, diffusion bonding or adhesive joining.

Different portions of the pump can be made of different ceramic materials. For example, the impeller housing 21 and forward pump housing 12 can be made of pyrolytic carbon, which is a conductor. Likewise, housing 36, pump back housing cover 38, and discharge tube 16 may be made of the same ceramic materials as the structural members 28 and 30 or may be made of the same structural materials as the forward pump housing 12.

The central rear of the impeller 20 comprises a journal bearing surface 40 for cooperating with a journal bearing surface 42 on structural member 28. It can be seen that structural member 28 is comprised of a number of contiguous pieces, each of which may be formed of a ceramic material. The ceramic journal bearing surfaces 40 and 42 may comprise a polycrystalline diamond coating.

It can be seen that a novel implantable blood pump has been shown and described, which blood pump is suitable for implantation in humans and which contains biocompatible, non-thrombogenic and corrosion resistant ceramic materials for alleviating eddy currents.

Although an illustrative embodiment of the invention has been shown and described, it is to be understood that various modifications and substitutions may be made by those skilled in the art without departing from the novel spirit and scope of the present invention.

What is claimed is:

1. A rotary blood pump, comprising:
    a pump housing;
    a rotor mounted for rotation within said housing, said rotor having an impeller;
    a rotor motor, said motor including a plurality of permanent magnets carried by said impeller and a motor stator located within said housing; and
    a structural member positioned between the impeller and stator comprising a biocompatible, corrosion resistant ceramic materials to reduce eddy current losses.

2. A rotary blood pump as defined in claim 1, in which said ceramic material is selected from the group consisting of aluminum oxide, zirconium oxide, yttria partial stabilized zirconia, magnesia-partial-stabilized zirconia, ceria-partial-stabilized zirconia, titanium oxide, magnesia, zirconia-toughened alumina, ruby, sapphire, single crystal alumina, cubic zirconia, quartz, fused silica, silicon nitride and aluminum nitride.

3. A rotary blood pump as defined in claim 1, in which said pump housing is sufficiently compact to be implantable in a human body.

4. A rotary blood pump as defined in claim 1, including radial magnetic bearings carried by said shaft portion and radial magnetic bearings carried by said housing.

5. A rotary blood pump as defined in claim 1, in which said structural member provides structural support and hermetical sealing, and in which said ceramic material is non-thrombogenic and electrically non-conductive.

6. A rotary blood pump as defined in claim 1, in which said pump housing also comprises a ceramic material.

7. A rotary blood pump as defined in claim 6, in which said pump housing ceramic material comprises pyrolytic carbon.

8. A rotary blood pump as defined in claim 1, in which said impeller includes an impeller housing having a journal bearing surface and said pump housing has a journal bearing surface for cooperating with said impeller housing journal bearing surface.

9. A rotary blood pump as defined in claim 8, in which said impeller journal bearing surface and said housing journal bearing surface comprise a polycrystalline diamond coating.

10. A rotary blood pump, comprising:
    a pump housing;
    a rotor mounted for rotation within said housing, said rotor having an impeller;
    a rotor motor, said motor including a plurality of permanent magnets carried by said impeller, a first motor stator positioned on one side of said impeller and a second motor stator positioned on an opposite side of said impeller;
    structural members positioned between the impeller and stators, said structural members comprising ceramic material to alleviate eddy current losses.

11. A rotary blood pump as defined in claim 10, in which said ceramic material is selected from the group consisting of aluminum oxide, zirconium oxide, yttria partial stabilized zirconia, magnesia-partial-stabilized zirconia, ceria-partial-stabilized zirconia, titanium oxide, magnesia, zirconia-toughened alumina, ruby, sapphire, single crystal alumina, cubic zirconia, quartz, fused silica, silicon nitride and aluminum nitride.

12. A rotary blood pump as defined in claim 10, in which said pump housing is sufficiently compact to be implantable in a human body.

13. A rotary blood pump as defined in claim 10, including radial magnetic bearings carried by said shaft portion and radial magnetic bearings carried by said housing.

14. A rotary blood pump as defined in claim 10, in which said structural member provides structural support and hermetical sealing, and in which said ceramic material is non-thrombogenic, electrically non-conducting and corrosion resistant.

15. A rotary blood pump as defined in claim 10, in which said pump housing also comprises a ceramic material.

16. A rotary blood pump as defined in claim 15, in which said pump housing ceramic material comprises pyrolytic carbon.

17. A rotary blood pump, comprising:
a pump housing comprising a ceramic material;
a rotor mounted for rotation within said housing; said rotor having an impeller;
a rotor motor, said motor including a plurality of permanent magnets carried by said impeller, a first motor stator positioned on one side of said impeller and a second motor stator positioned on an opposite side of said impeller;
structural members positioned between the impeller and stators, said structural members comprising ceramic material to reduce eddy current losses that is selected from the group consisting of aluminum oxide, zirconium oxide, yttria partial stabilized zirconia, magnesia-partial-stabilized zirconia, ceria-partial-stabilized zirconia, titanium oxide, magnesia, zirconia-toughened alumina, ruby, sapphire, single crystal alumina, cubic zirconia, quartz, fused silica, silicon nitride and aluminum nitride;
radial magnetic bearings carried by said shaft portion;
radial magnetic bearings carried by said housing;
said structural members providing structural support and hermetical sealing; and
said pump housing being sufficiently compact to be implantable in a human body.

18. A method for reducing eddy current losses in a rotary blood pump, which comprises the steps of:
providing a pump housing;
providing a rotor for rotation within said housing, said rotor having an impeller;
providing a rotor motor which includes a plurality of permanent magnets carried by said impeller and a motor stator; and
positioning between said impeller and stator a structural member comprising a biocompatible, corrosion resistant ceramic material.

19. A method as defined in claim 18, in which the pump housing providing step comprises the step of providing a pump housing comprising a ceramic material.

20. A method as defined in claim 19, including the step of sizing the rotary blood pump to be compact enough for implantation in a human body.

* * * * *